US00PP36107P2

(12) United States Plant Patent
Smit

(10) Patent No.: US PP36,107 P2
(45) Date of Patent: Sep. 10, 2024

(54) ***PEPEROMIA* PLANT NAMED 'EC-PEPE-2202'**

(50) Latin Name: *Peperomia angulata*
Varietal Denomination: EC-PEPE-2202

(71) Applicant: Eden Collection, BV, Sappemeer (NL)

(72) Inventor: Obed Smit, Sappemeer (NL)

(73) Assignee: Eden Collection (NL)

( * ) Notice: Subject to any disclaimer, the term of this patent is extended or adjusted under 35 U.S.C. 154(b) by 0 days.

(21) Appl. No.: 18/373,995

(22) Filed: Sep. 28, 2023

(51) Int. Cl.
*A01H 6/00* (2018.01)
*A01H 5/02* (2018.01)

(52) U.S. Cl.
USPC ..... Plt./373

(58) Field of Classification Search
USPC ..... Plt./373
CPC ..... A01H 6/00; A01H 5/12
See application file for complete search history.

*Primary Examiner* — Keith O. Robinson
(74) *Attorney, Agent, or Firm* — Cassandra Bright

(57) ABSTRACT

A new and distinct cultivar of *Peperomia* plant named 'EC-PEPE-2202' is disclosed, characterized by distinctive bright green foliage with a bronze coloration to the upper surface, especially on young foliage. Leaves are strong and glossy with bright green parallel venation. The new variety is a *Peperomia*, typically used as an ornamental plant.

3 Drawing Sheets

Latin name of the genus and species: *Peperomia angulata.*

Variety denomination: 'EC-PEPE-2202'.

BACKGROUND OF THE INVENTION

The new cultivar is a product of a planned breeding program to produce distinct and better performing *Peperomia* varieties. The new variety was selected as a seedling resulting from the crossing of the unpatented proprietary variety *Peperomia quandrangularis* '1902' as the female parent, and the unpatented *Peperomia angulata* 'Rocca Verde' as the male parent. The crossing was made by the inventor, Obed J. Smit, a citizen of the Netherlands in 2019. 'EC-PEPE-2202' was selected by the inventor in 2020 at a commercial greenhouse in Sappemeer, the Netherlands.

Asexual reproduction of the new cultivar 'EC-PEPE-2202' by terminal cuttings was first performed in Sappemeer, the Netherlands at a commercial greenhouse in April of 2020, and has shown that the unique features of this cultivar are stable and reproduced true to type through successive generations.

SUMMARY OF THE INVENTION

The cultivar 'EC-PEPE-2202' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2202'. These characteristics in combination distinguish 'EC-PEPE-2202' as a new and distinct *Peperomia* cultivar:

1. Distinctive bright green foliage with a bronze coloration to the upper surface, especially on young foliage.
2. Very bright green parallel venation.
3. Strong, glossy leaves.

PARENT COMPARISON

Plants of the new cultivar 'EC-PEPE-2202' are similar to plants of the female parent in most horticultural characteristics, however, plants of the new cultivar 'EC-PEPE-2202' differ from in the following characteristics:

1. Leaves of the new variety are bright green with a distinct bronze coloration on the upper surface; foliage of the seed parent is dark green.
2. Venation color of the new variety is brighter yellow-green than venation color of the seed parent.

Plants of the new cultivar 'EC-PEPE-2202' are similar to plants of the pollen parent in most horticultural characteristics, however, plants of the new cultivar 'EC-PEPE-2202' differ in the following characteristics:

1. Leaves of the new variety are bright green with a distinct bronze coloration on the upper surface; foliage of the pollen parent is dark green.
2. Venation color of the new variety is bright yellow-green; venation color of the pollen parent is dark green.
3. The new variety has a more upright habit than the pollen parent which is somewhat pendulous.
4. Foliage of the new variety is oval shaped; foliage of the pollen parent is narrower, more elliptical.

COMMERCIAL COMPARISON

Plants of the new cultivar 'EC-PEPE-2202' are similar to plants of the commercial variety *Peperomia* 'Rocco Scuro', unpatented. However, plants of the new cultivar differ in the following characteristics:

1. Leaves of the new variety are bright green with a distinct bronze coloration on the upper surface; foliage of this comparator is solid dark green.
2. The new variety has a more upright habit than this comparator, which is somewhat pendulous.

3. Foliage of the new variety is oval shaped; foliage of this comparator is rounder, more orbicular.

BRIEF DESCRIPTION OF THE PHOTOGRAPHS

The accompanying photograph in FIG. 1 illustrates in full color a typical plant of 'EC-PEPE-2202' grown in a greenhouse. The plant is approximately 20 weeks of age.

Figure 1:
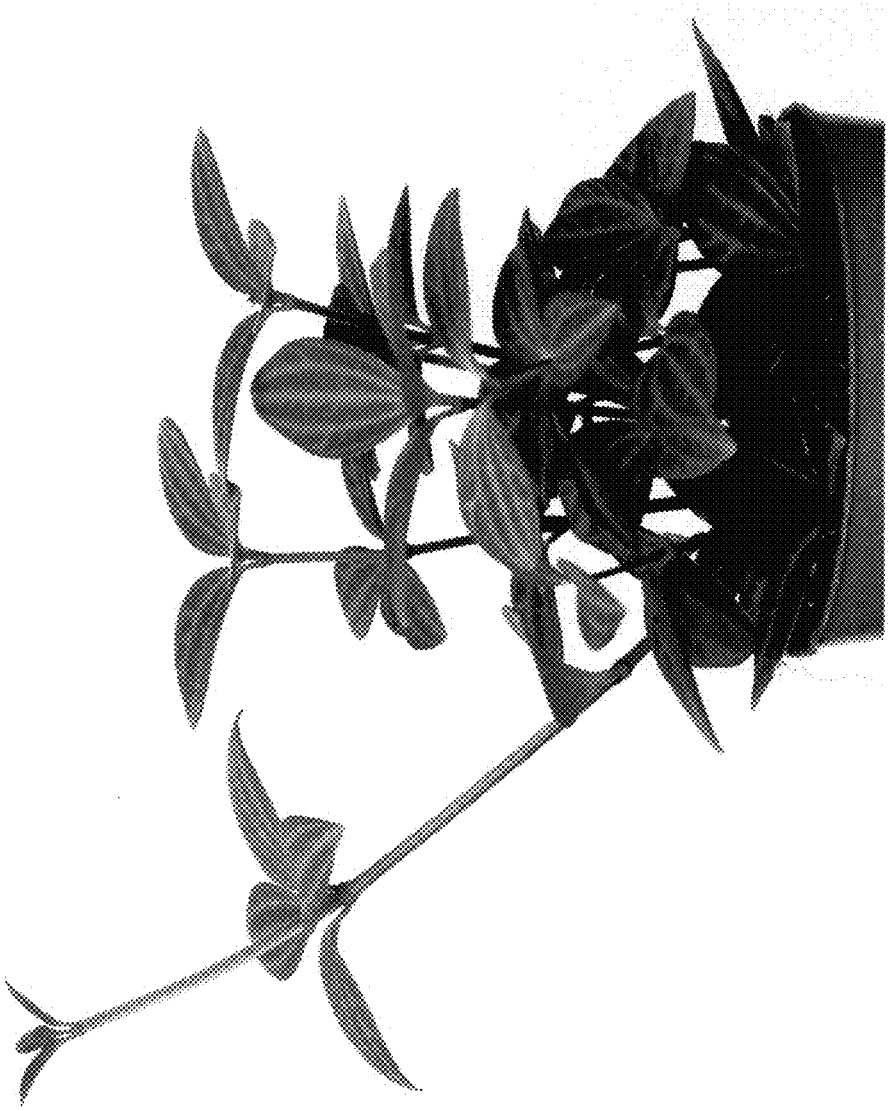
Figure 2:
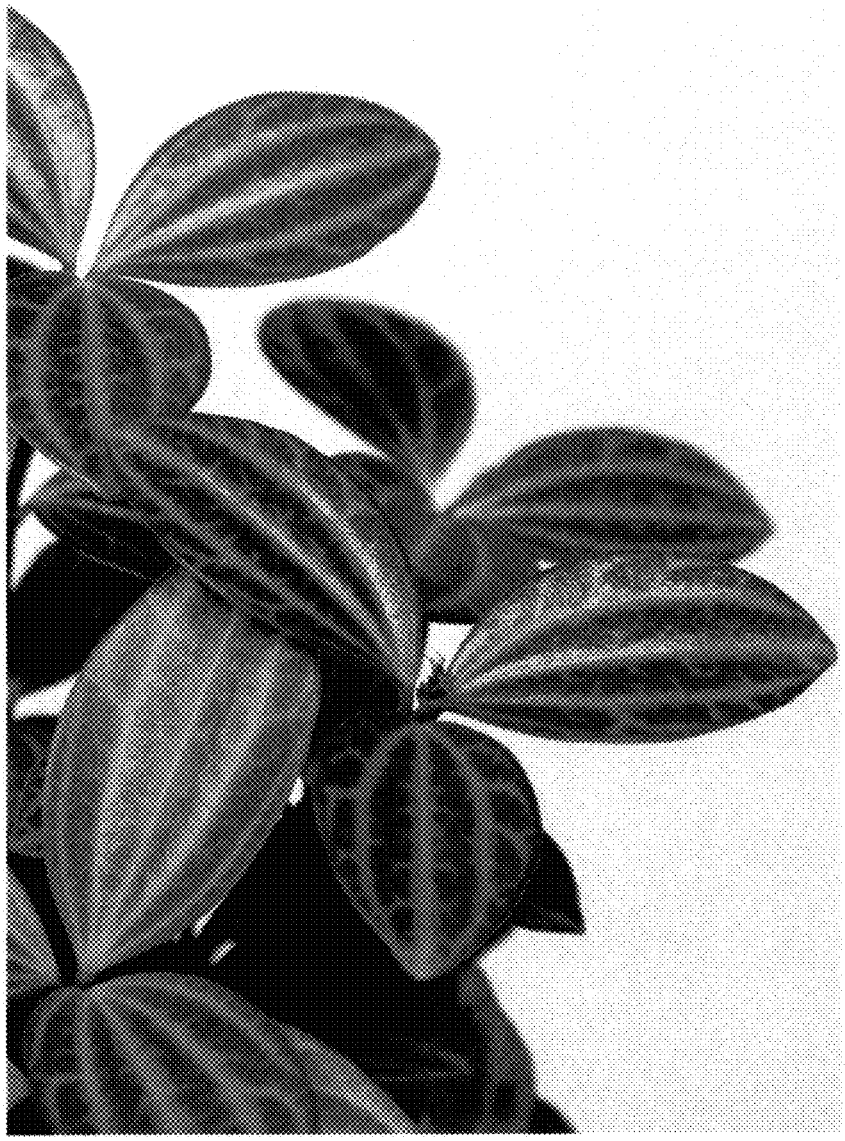
FIG. 2 illustrates a close up of the foliage.
Figure 3:
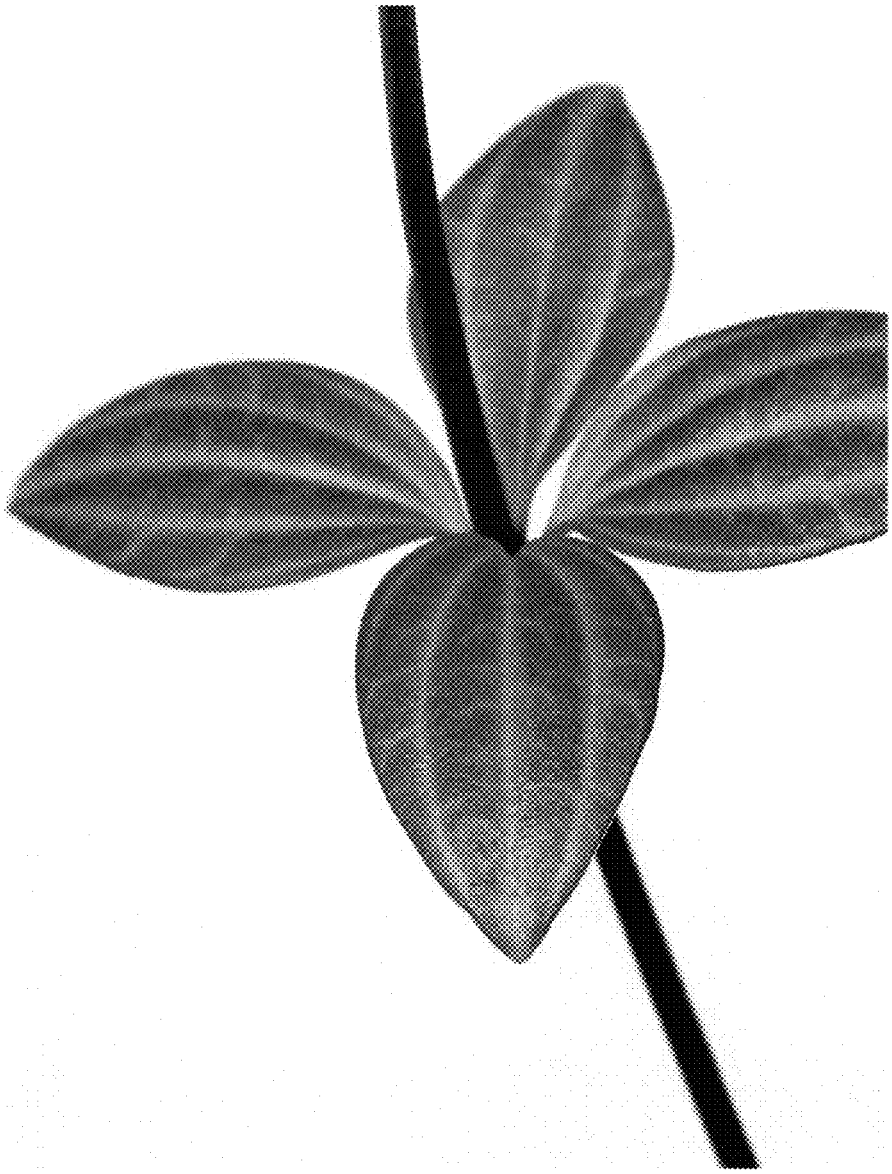
FIG. 3 illustrates a close up of young foliage, having a slightly bronze cast.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-2202' plants at 20 weeks of age, grown in a greenhouse in Sappemeer, the Netherlands during December. The growing temperature ranged from 17° C. to 20° C. at night to 19° C. to 21° C. during the day. Measurements and numerical values represent averages of typical flowering types.

Botanical classification: *Peperomia angulata* 'EC-PEPE-2202'.

PROPAGATION

Time to initiate roots: About 7 to 10 days at approximately 20° C.

Description of roots: Fine, non-fibrous, moderately dense, freely branching. White in color, not accurately measured with R.H.S. chart.

PLANT

Age of plant described: Approximately 20 weeks planted 4 cuttings per pot in a 10 cm pot.

Plant type: Perennial potted plant.

Growth habit: Upright and slightly outward. Rosettes of leaves, forming very short, thick stems. No lateral branches present.

Plant spread: Approximately 11.2 cm.

Height: 13 cm to top of foliar plane.

Growth rate: Moderate.

Plant vigor: Moderate.

Pinching: Pinching not required.

Number of primary (main) branches per plant: Average 3.

Main branches:

*Length*.—Average: 10.6 cm.

*Diameter*.—Average: 0.25 cm.

Internode length: Average: Less than 3.7 cm.

Appearance and shape: Succulent, angulate, 5 sided.

Luster: Glossy.

Aspect/angle from vertical: Average angle: 25°; varying between 0° to 50°.

Strength: Moderately strong.

Color:

*Developing*.—RHS Yellow-Green 151A, flushed Greyed-Red 181A and 181B, both colors present.

*Mature*.—RHS Yellow-Green 152A, heavily flushed Greyed-Red 181A.

*At internodes*.—RHS Yellow-Green 146D.

Pubescence: None.

Plant fragrance: None.

FOLIAGE

Leaf:

*Arrangement*.—Whorled, whorls of 3 or 4.

*Quantity leaves per main branch*.—Average 8.

*Average length*.—3.7 cm.

*Average width*.—2.3 cm.

*Shape of blade*.—Ovate.

*Apex*.—Acute.

*Base*.—Broad attenuate.

*Margin*.—Entire.

*Texture of top surface*.—Glabrous, smooth, moderately leathery, slightly to moderately bullate.

*Texture of bottom surface*.—Glabrous, smooth, moderately leathery.

*Pubescence*.—None.

*Luster, upper side*.—Glossy.

*Luster, under side*.—Matte.

*Color*.—Young foliage upper side: RHS Yellow-green; 148A, flushed 164A veined lighter; 144B. Young foliage under side: RHS Yellow-green; 148D. Mature foliage upper side: RHS Green N137 and 139A. Mature foliage under side: RHS Yellow-Green 146C mixed with 147D.

*Venation*.—Pattern: Parallel, 3 conspicuous main veins. Moderately furrowed. Venation color upper side: RHS Green 143B. Venation color under side: RHS Yellow-Green 147C.

*Petiole*.—Average Length: 0.35 cm. Diameter: 0.15 cm. Texture: Glabrous, smooth. Luster: Both sides matte. Strength: Moderate. Color, upper side: RHS Yellow-Green 148A. Color, under side: RHS Yellow-Green 148B.

FLOWER

Flowering not observed to date.

OTHER CHARACTERISTICS

Seeds and fruits: None observed to date.

Disease/pest resistance: No increased nor decreased resistance nor susceptibility to normal diseases and pests of *Peperomia* has been observed. Typical diseases found in *Peperomia* include ring spot (*Peperomia* ring spot virus), *Phytophthora* rot (*Phytophthora pabivora, P. nicotiane* var *Parasitica*) and various *Pythium* species. Insect pests commonly found on *Peperomia* are mealybugs (various *Pseudococcidae*) and mites (*Phytonemus pallidus, Polyphagotarsonemus latus, Tarsonemus confusus*). Various species of *Thysanoptera* can also be found on *Peperomia*.

Temperature tolerance: Tolerates temperatures up to 40° C. Hardy to USDA zones 10 to 12.

What is claimed is:

1. A new and distinct cultivar of *Peperomia* plant named 'EC-PEPE-2202' as herein illustrated and described.

* * * * *